(12) United States Patent
Bille et al.

(10) Patent No.: US 8,529,557 B2
(45) Date of Patent: Sep. 10, 2013

(54) SYSTEM AND METHOD FOR STRAY LIGHT COMPENSATION OF CORNEAL CUTS

(75) Inventors: Josef F. Bille, Heidelberg (DE); Frieder Loesel, Mannheim (DE)

(73) Assignee: Technolas Perfect Vision GmbH (DE)

( * ) Notice: Subject to any disclaimer, the term of this patent is extended or adjusted under 35 U.S.C. 154(b) by 1503 days.

(21) Appl. No.: 12/130,937

(22) Filed: May 30, 2008

(65) Prior Publication Data

US 2009/0299346 A1    Dec. 3, 2009

(51) Int. Cl.
*A61B 18/18* (2006.01)
*A61F 9/008* (2006.01)

(52) U.S. Cl.
CPC ... *A61F 9/00804* (2013.01); *A61F 2009/00872* (2013.01)
USPC .......................................................... 606/5

(58) Field of Classification Search
None
See application file for complete search history.

(56) References Cited

U.S. PATENT DOCUMENTS

| | | | |
|---|---|---|---|
| 4,579,430 A | 4/1986 | Bille | |
| 4,669,466 A | 6/1987 | L'Esperance | |
| 4,770,172 A | 9/1988 | L'Esperance, Jr. | |
| 4,838,631 A | 6/1989 | Chande et al. | |
| 5,533,997 A | 7/1996 | Ruiz | |
| 5,777,719 A | 7/1998 | Williams et al. | |
| 6,002,484 A | 12/1999 | Rozema et al. | |
| 6,050,687 A | 4/2000 | Bille et al. | |
| 6,086,204 A | 7/2000 | Magnante | |
| 6,095,651 A | 8/2000 | Williams et al. | |
| 6,097,522 A | 8/2000 | Maerki et al. | |
| 6,382,797 B1 | 5/2002 | Bille et al. | |
| 6,730,074 B2 * | 5/2004 | Bille et al. | 606/5 |
| 7,238,176 B2 * | 7/2007 | Loesel et al. | 606/5 |
| 2004/0044355 A1 | 3/2004 | Nevyas | |

FOREIGN PATENT DOCUMENTS

| | | |
|---|---|---|
| EP | 1364632 A1 | 11/2003 |
| EP | 1591087 A1 | 11/2005 |
| WO | 2005011547 A1 | 2/2005 |
| WO | 2007022993 A2 | 3/2007 |
| WO | 2008030698 A2 | 3/2008 |

* cited by examiner

*Primary Examiner* — Bethany Barham
(74) *Attorney, Agent, or Firm* — Nydegger & Associates

(57) ABSTRACT

A system and method to compensate for the deformation of an eye requires calculation of an induced deformation angle $\Psi$, wherein the deformation is intentionally induced during laser surgery by a contact lens, and a refraction angle $\phi$. Specifically, during laser surgery, the cornea of an eye is typically stabilized by a contact lens. This deforms the cornea. When the contact lens is removed after the surgery, the cornea recovers from the deformation. For the present invention, the angle $\Psi$ is calculated, and corrected by the angle $\phi$, so that surfaces altered during surgery (e.g. by LIOB) will become substantially parallel to incoming light in the eye, after the contact lens has been removed after surgery.

13 Claims, 2 Drawing Sheets

SYSTEM AND METHOD FOR STRAY LIGHT COMPENSATION OF CORNEAL CUTS

FIELD OF THE INVENTION

The present invention pertains generally to systems and methods for performing ophthalmic laser surgery. More particularly, the present invention pertains to systems and methods for performing ophthalmic surgery that alter stromal tissue in the cornea by Laser Induced Optical Breakdown (LIOB). The present invention is particularly, but not exclusively, useful when LIOB is used to weaken corneal tissue on selected surfaces in the cornea for subsequent reshaping of the eye by intraocular pressure in the eye.

BACKGROUND OF THE INVENTION

Light effectively enters an eye substantially parallel to the eye's visual axis. In a normal eye, light is refracted inside the eye (i.e. at the anterior surface of the eye) so it will be incident on the retina in a manner that allows for the creation of a visual image. More specifically, it is known that the refraction of light at the anterior surface of an eye directs the incident light toward a common point on the eye's visual axis. Furthermore, based on the anatomical structure of an eye, this point is calculated to be generally located at a distance approximately 20 mm from the eye's anterior surface. Accordingly, the incident light will have an angle of refraction "$\phi$" that depends directly on where the light is incident on the eye's anterior surface. Geometrically, when the light is incident on the anterior surface at a distance "s" from the eye's visual axis, the angle "$\phi$" is equal to arc sin s/20. Importantly, light that is incident on the anterior surface of the cornea of an eye, at a distance "s" from the visual axis, will be refracted and directed along the surface of what is hereinafter referred to as a "refraction cone" or "refraction conical surface". In each instance, this refractive cone is centered on the visual axis and has a decreasing taper in the posterior direction. The angle of taper for the refraction cone is equal to the refraction angle "$\phi$" (i.e. arc sin s/20).

When incoming light is not refracted in the manner noted above, or is otherwise scattered in some way, visual distortions or hazy (cloudy) sensations can sometimes result in the image. It happens that these sensations may be caused by the very surgical attempts that were made to correct the underlying vision defect.

As recently disclosed in a U.S. patent application for an invention entitled "Computer Control for Bio-Mechanical Alteration of the Cornea," which was filed on "Jan. 18, 2008," and which is assigned to the same assignee as the present invention, the reshaping of a cornea to correct visual defects can be effectively accomplished by performing LIOB over all or portions of substantially cylindrical-shaped surfaces in the cornea. As implied above, if these surfaces do not account for the refraction angle "$\phi$" (i.e. the surfaces do not eventually conform with the appropriate refraction cone) it is possible they will cause refractions that result in stray light being generated. As indicated above, this can cause unwanted visual sensations. Specifically, it is known that, under certain lighting conditions, this stray light will introduce a hazy or cloudy sensation into a patient's perceived visual image.

The elimination or effective minimization of stray light in the eye is, in large part, dependent on ensuring that abnormal refractive surfaces are not presented by the cornea. Stated differently, in order to avoid the introduction of stray light, when a surgical procedure is employed to produce so-called cylindrical cuts it is important that the surfaces (i.e. cuts) created during the procedure are effectively and properly oriented on a refraction cone relative to the visual axis; after the surgery. The issue then turns to how these surfaces are created, and how they are oriented during their creation.

In essence, any surface that is created by "cuts" into intrastromal corneal tissue, may cause stray light to be introduced. LIOB is a well known method for creating these cuts. Other known procedures, however, may also result in such "cuts." Specifically, for one, when tissue is repeatedly impacted by a sequence of multiple laser pulses, the result can be a compromise of the tissue. A sufficient number of such impacts can then effectively result in the creation of a "cut." This can happen, even though the multiple laser pulses (e.g. femtosecond laser pulses) each has an energy level that is below the threshold for LIOB. Still, an unwanted consequence may be the introduction of stray light. With the above in mind, reference to LIOB in the disclosure below should be taken to include not only LIOB, as generally defined, but also other laser surgical procedures that create "cuts" to thereby create an intrastromal surface in the cornea For purposes of ophthalmic surgery, in order to perform any LIOB, or LIOB-type, surgical procedure it is typically necessary to first stabilize the eye. In most instances, this eye stabilization is accomplished by engaging the anterior surface of the eye with a contact lens. To ensure an effective engagement, however, the contact lens needs to have a radius of curvature "$R_c$" that is greater than the anatomical radius of curvature "R" of the eye. As a consequence, when a contact lens is engaged with an eye, the eye and its cornea become deformed. LIOB is therefore performed on a deformed cornea. When the contact lens is then removed from the eye, the eye (and cornea) will naturally recover from the deformation. In this case, the predominant recovery forces will be provided by intraocular pressure (IOP) in the eye. To ensure that surfaces created by LIOB will become appropriately oriented relative to the visual axis of the eye after surgery, deformation of the cornea during the LIOB procedure requires compensation. And, this compensation needs correction by the refraction angle "$\phi$" discussed above.

In light of the above it is an object of the present invention to provide for an effective alignment of LIOB created surfaces parallel to the visual axis, after a surgical procedure. Another object of the present invention is to provide for systems and methods that will compensate for anatomical deformations of a cornea during LIOB surgery by predicting the recovery trends of the cornea after the surgery has been performed. Still another object of the present invention is to provide for systems and methods for minimizing stray light caused by the LIOB of tissue on surfaces inside a cornea of a patient that are easy to employ and comparatively cost effective.

SUMMARY OF THE INVENTION

In accordance with the present invention, a system and method are provided for minimizing stray light that may be caused when stromal tissue in a cornea is altered by Laser Induced Optical Breakdown (LIOB). More specifically, the main object of the present invention is to compensate for potential adverse visual sensations (e.g. haziness or cloudiness in the vision of a patient) that can result when stray light is refracted from photoaltered tissue inside the cornea. When LIOB is accomplished to specifically create so-called cylindrical surfaces in the cornea, this compensation is accomplished by creating LIOB surfaces that will undergo a predictable transition after surgery. Specifically, it is intended that these surfaces become aligned on a defined refraction cone, when the stabilizing contact lens is removed.

As envisioned for the present invention, a femtosecond laser beam is directed from a laser unit through the contact lens to perform LIOB of corneal tissue on selected surface(s). This LIOB is accomplished over at least a portion of a conical surface in the cornea. As a consequence of the predetermined deformation of the cornea, the conical surface will need to be inclined at an induced deformation angle $\Psi$ relative to the visual axis. And, the induced deformation angle $\Psi$ will need to include correction by the refraction angle $\phi$. It happens that the resultant conical surface will have an increasing taper in a posterior direction along the visual axis of the eye.

After surgery, when the contact lens is removed from the eye, the eye will recover from the deformation caused by the contact lens. With this recovery, there will be a transition from the conical surface (i.e. a cutting conical surface), whereon LIOB was performed during surgery, to the surface of the refraction cone that is centered on the visual axis. This transition causes the induced deformation angle $\Psi$ to become effectively zero, and causes the deformation angle $\phi$ continue to minimize the introduction of stray light into the vision of the patient.

For the present invention, several values are of interest. For instance, the anterior surface of the eye has an anatomical radius of curvature "R" that is equal to approximately 7.8 mm. The contact surface of the contact lens has a radius of curvature "$R_c$" that is equal to approximately 10 mm. As for the induced deformation angle $\Psi$, its calculation starts with the selection of a reference point that is located at a radial distance "s" from the visual axis. The angle $\Psi$ can then be taken as being equal to arc sin s/R minus arc sin s/$R_c$. As envisioned for the present invention, "s" will normally be less than two millimeters, the angle $\Psi$ will be less than twenty five degrees, and the laser unit will generate a femtosecond laser beam. Recall, the deformation cone will have a taper angle $\phi$ (i.e. refraction angle) that is equal to arc sin s/20.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
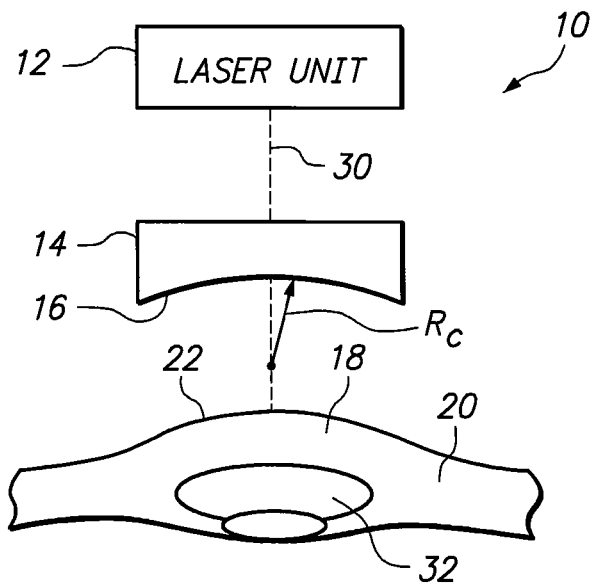
FIG. 1 is a schematic view of a system of the present invention.

Referring initially to FIG. 1, a system for minimizing stray light caused by LIOB of stromal tissue is shown and is generally designated 10. As shown, the system 10 includes a laser unit 12 and a contact lens 14. Also, the contact lens 14 is shown to have a contact surface 16 that is defined by its radius of curvature "$R_c$". FIG. 1 also shows a cornea 18 of an eye 20 positioned for laser surgery. During this surgery, the contact lens 14 is positioned against the anterior surface 22 of the cornea 18 to stabilize the eye 20.

As envisioned for the present invention, when the contact surface 16 of contact lens 14 is positioned against the anterior surface 22 of the cornea 18, the cornea 18 becomes deformed. This effectively changes the curvature of the anterior surface 22. Specifically, this involves a change from the natural, anatomical radius of curvature "R" of the anterior surface 22 of the cornea 18 to the radius of curvature "$R_c$" of the contact lens 14. This deformation is shown graphically in FIG. 2.

Figure 2:
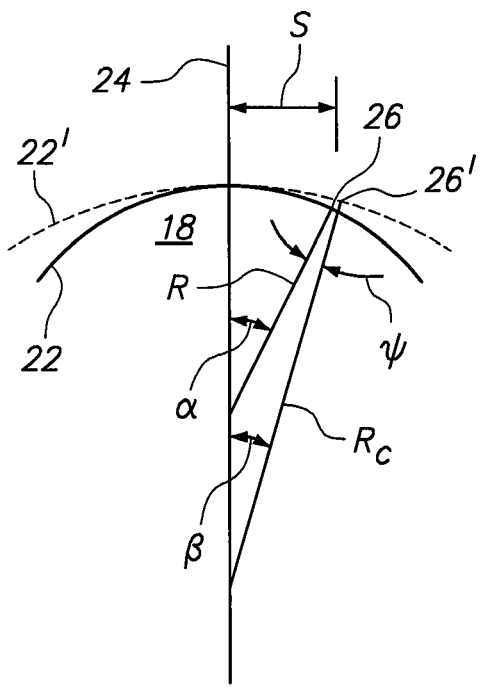
FIG. 2 is a graphic illustration of the geometrical relationships of respective radii of curvature of a cornea and of a contact lens relative to the visual axis of the eye and to the anterior surface of the eye during and after contact with a contact lens.

In FIG. 2, the natural anatomical anterior surface 22 of cornea 18, with a radius of curvature "R", is shown before its engagement with the contact lens 14. A deformed anterior surface 22' for the cornea 18, during its engagement with the contact lens 14, is shown with an altered radius of curvature "$R_c$". FIG. 2 also shows the respective radii of curvature "R" and "$R_c$" relative to the visual axis 24 of the eye 20. Further, a reference point 26 is shown on the anterior surface 22 with the reference point 26 being located at a distance "s" from the visual axis 24. Also, a reference point 26' is shown on the anterior surface 22'. For purposes of the present invention, the reference point 26' is also considered to be located at the distance "s" from the visual axis 24. As will be appreciated by the skilled artisan, the distance "s" is variable, and will depend on specific requirements of the particular surgical procedure that is to be performed.

Depending on the value of "s", the radius of curvature "R" of anterior surface 22 will make an angle $\alpha$ with the visual axis 24. This angle $\alpha$ has a value equal to arc sin s/R. Similarly, the radius of curvature "$R_c$" will make an angle $\beta$ with the visual axis 24 that has a value equal to arc sin s/$R_c$. Geometrically, it can be shown that an induced deformation angle $\Psi$ (i.e. the change in angle of a radius of curvature relative to the visual axis 24 that is caused by a deformation of the cornea 18) is equal to the angle $\alpha$ minus the angle $\beta$. In summary:

$\alpha$=arc sin $s/R$;

$\beta$=arc sin $s/R_c$; and $\Psi$=$\alpha$-$\beta$

Importantly, the induced deformation angle $\Psi$ is a measure of the recovery that the cornea 18 will experience when contact lens 14 is removed from the cornea 18 after a surgical procedure. The consequence of this is best seen in FIG. 3.

Figure 3:
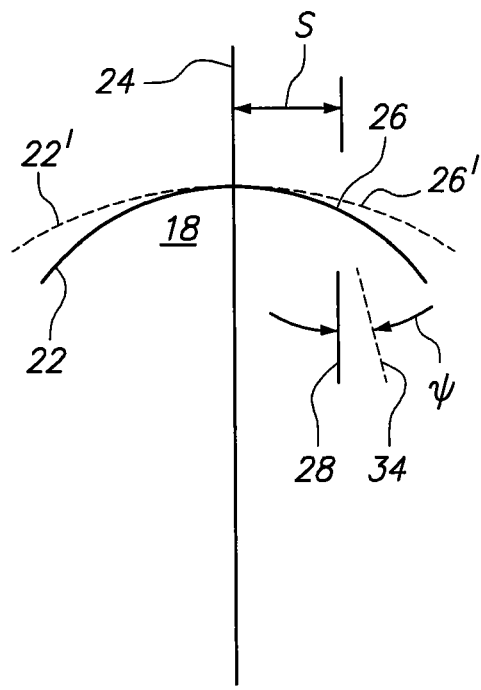
FIG. 3 is a graphic illustration of the recovery of an LIOB surface (i.e. cut) after a removal of a contact lens from the anterior surface of an eye.

In FIG. 3, line 28 represents a surface (i.e. cut) that is substantially parallel to the visual axis 24 of the eye 20. It can be appreciated that this line 28, if continued around the visual axis 24, would result in a substantially cylindrical surface that is centered on the visual axis 24.

As noted above, however, when a laser beam 30 (see FIG. 1) is directed into the cornea 18 during refractive surgery to perform Laser Induced Optical Breakdown (LIOB) of tissue in the cornea 18, the eye 20 is typically being stabilized by the contact lens 14. Further, as disclosed above with reference to FIG. 2, when the contact lens 14 is removed from the cornea 18 after surgery, the cornea 18 will tend to recover to its anatomical configuration (i.e. anterior surface 22). This recovery is due primarily to intraocular pressure in the anterior chamber 32 of the eye 20 (see FIG. 1).

In order to compensate for the recovery of the cornea 18 after LIOB surgery, LIOB needs to be performed in a manner that accounts for the induced deformation angle Ψ. It also needs to be corrected by the refraction angle φ. Insofar as the deformation is concerned (i.e. the angle Ψ), in order to eventually obtain an orientation for a cut (i.e. LIOB surface) along the line 28, performance of the LIOB needs to be accomplished along the line 34 (see FIG. 3). To do this in actual practice, LIOB needs to be performed over a cutting conical surface that is inclined relative to the visual axis 24. As indicated by the line 34, such a conical surface will have an increasing taper in the posterior direction from the anterior surface 22. After surgery, and after the contact lens 14 is removed from the cornea 18, the angle Ψ becomes substantially zero. All of this, however, preferably involves the refraction angle φ.

Figure 4:
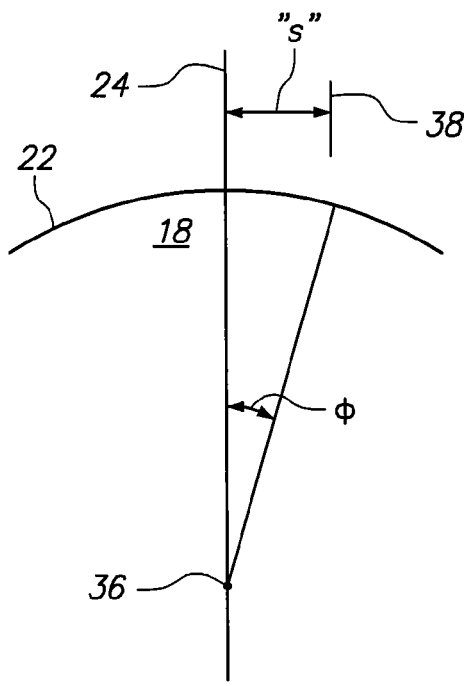
FIG. 4 is a graphic illustration showing the relationship of a refraction angle "$\phi$" relative to the geometry of an eye.

Calculation of the refraction angle φ, for correcting the induced deformation angle Ψ, will be best appreciated with reference to FIG. 4. FIG. 4 indicates that when light enters the eye from a direction substantially parallel to the visual axis 24 (e.g. along a line 38), it will be refracted at the anterior surface 22 of the cornea 18 through a refraction angle φ. The refracted light will then be directed toward a point 36 on the visual axis 24. Anatomically, the point 36 is approximately twenty eight mm from the anterior surface 22 of the cornea 18. This measurement is substantially constant for all patients. The magnitude of the refraction angle φ, however, will vary as it is directly dependent on the distance "s" from the visual axis 24 where incoming light is incident on the anterior surface 22. Specifically, the magnitude of the angle φ will equal arc sin s/20. Thus, for a short distance "s", the angle φ will be very small. When "s" is equal to about two millimeters, however, the angle φ will be about five degrees.

Figure 5:
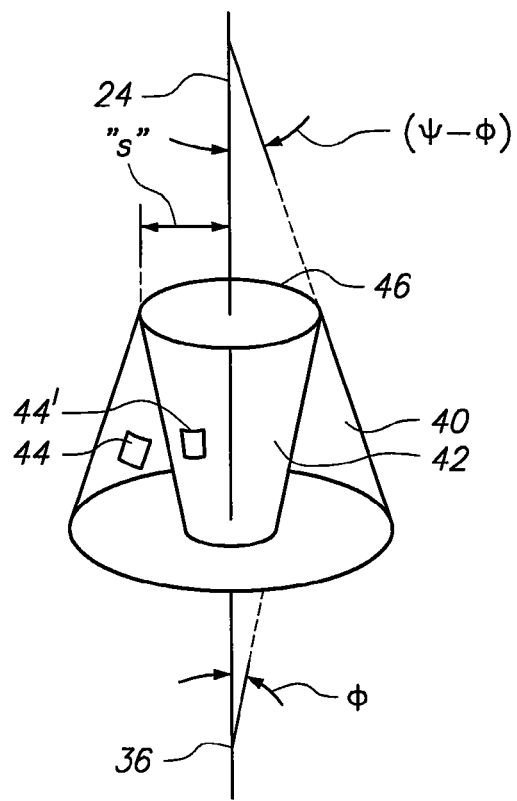
FIG. 5 is a perspective presentation of the surface of a cutting cone in the cornea (where LIOB cuts are made) relative to a refraction cone (where the LIOB tissue will eventually be oriented).

Operation of the system 10 will, perhaps, be best appreciated with reference to FIG. 5. In FIG. 5 the induced deformation angle Ψ, and the refraction angle φ, are as disclosed and defined above. Further, the distance "s" will be specifically determined by the requirements of the particular LIOB surgical procedure that is to be conducted. The calculations can then be made and the procedure can be conducted to account for deformations caused by the use of a contact lens 14 (i.e. calculate the angle Ψ), and to correct for refractions (i.e. calculate the angle φ).

FIG. 5 shows both a cutting cone 40, and a refraction cone 42 as contemplated by the present invention. As shown, these cones 40 and 42 intersect each other at the ring 46. Importantly, this theoretical ring 46 is located on the anterior surface 22 of a cornea 18, and is selected to be at the distance "s" from the visual axis 24. As a consequence, LIOB on a portion 44 of the conical surface of the cutting cone 40 (i.e. LIOB performed during a procedure while the contact lens 14 deforms the cornea 18) will result in a repositioning of the portion 44' onto the conical surface of the refraction cone 42 after the surgical procedure (i.e. when the contact lens 14 has been removed from the cornea 18). In order to accomplish this, the cutting conical surface of the cutting cone 40 needs to be tapered, relative to the visual axis, at an angle (Ψ−φ).

While the particular System and Method for Stray Light Compensation of Corneal Cuts as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for minimizing stray light caused by the creation of surfaces in intrastromal tissue of a cornea of an eye of a patient which comprises:
   a contact lens having a contact surface having a radius of curvature "$R_c$" equal to approximately 10 mm, wherein the contact surface is engaged with the anterior surface of the eye, wherein the anterior surface of the eye has a radius of curvature "R" equal to approximately 7.8 mm and the contact lens is positioned thereon to introduce a predetermined deformation of the cornea;
   a laser unit for directing a laser beam through the contact lens to alter corneal tissue over at least a portion of a cutting conical surface in the cornea, with the cutting conical surface having an increasing taper in a posterior direction along the visual axis of the eye, and wherein a reference point is selected on the anterior surface of the eye at a radial distance "s" from the visual axis, and wherein the cutting conical surface is inclined to compensate for the predetermined deformation with an induced deformation angle Ψ, with Ψ equal to arc sin s/R minus arc sin s/$R_c$, and to compensate for refraction with an angle φ, with φ equal to arc sin s/20; and
   a means for removing the contact lens from the eye for recovery of the eye from the deformation caused by the contact lens, with a consequent transition from the cutting conical surface to a refraction conical surface, where the induced deformation angle Ψ becomes effectively zero to minimize an introduction of stray light into the vision of the patient.

2. A system as recited in claim 1 wherein "s" is less than about two millimeters, wherein the angle Ψ is less than twenty five degrees, wherein the angle φ is less than five degrees, and wherein the laser unit generates a femtosecond laser beam.

3. A system as recited in claim 1 wherein an intersection between the cutting conical surface and the anterior surface of the eye is at a radial distance "s" from the visual axis.

4. A system as recited in claim 3 wherein a plurality of conical surfaces are involved, and each conical surface has a respective value for "s".

5. A system as recited in claim 3 wherein "s" is less than about two millimeters.

6. A system as recited in claim 1 wherein the laser unit generates a femtosecond laser beam.

7. A system for minimizing stray light caused by the creation of surfaces in intrastromal tissue of a cornea of an eye of a patient which comprises:
   a contact lens having a contact surface, wherein the contact surface is engaged with the anterior surface of the eye to introduce a predetermined deformation of the cornea;
   a laser unit for directing a laser beam through the contact lens to alter corneal tissue over at least a portion of a cutting conical surface in the cornea, with the cutting conical surface having an increasing taper in a posterior direction along the visual axis of the eye, and wherein an intersection between the cutting conical surface and the anterior surface of the eye is at a radial distance "s" from the visual axis, and wherein the cutting conical surface is inclined to compensate for the predetermined deformation with an induced deformation angle Ψ and to compensate for refraction with an angle Φ; and
   a means for removing the contact lens from the eye for recovery of the eye from the deformation caused by the contact lens, with a consequent transition from the cutting conical surface to a refraction conical surface, where the induced deformation angle Ψ becomes effectively zero to minimize an introduction of stray light into the vision of the patient.

8. A system as recited in claim 7 wherein the anterior surface of the eye has a radius of curvature "R" and the contact surface of the contact lens has a radius of curvature "$R_c$", wherein R is equal to approximately 7.8 mm, and $R_c$ is equal to approximately 10 mm.

9. A system as recited in claim 8 wherein a reference point is selected on the anterior surface of the eye at the distance "s" from the visual axis, wherein the angle Ψ is equal to arc sin s/R minus arc sin $s/R_c$, and wherein the refraction angle φ is equal to arc sin s/20.

10. A system as recited in claim 9 wherein "s" is less than about two millimeters, wherein the angle Ψ is less than twenty five degrees, wherein the angle φ is less than five degrees, and wherein the laser unit generates a femtosecond laser beam.

11. A system as recited in claim 7 wherein a plurality of conical surfaces are involved, and each conical surface has a respective value for "s".

12. A system as recited in claim 7 wherein "s" is less than about two millimeters.

13. A system as recited in claim 7 wherein the laser unit generates a femtosecond laser beam.

\* \* \* \* \*